Oct. 14, 1952 R. L. WHEELER Plant Pat. 1,137
CAMELLIA PLANT
Filed April 26, 1950
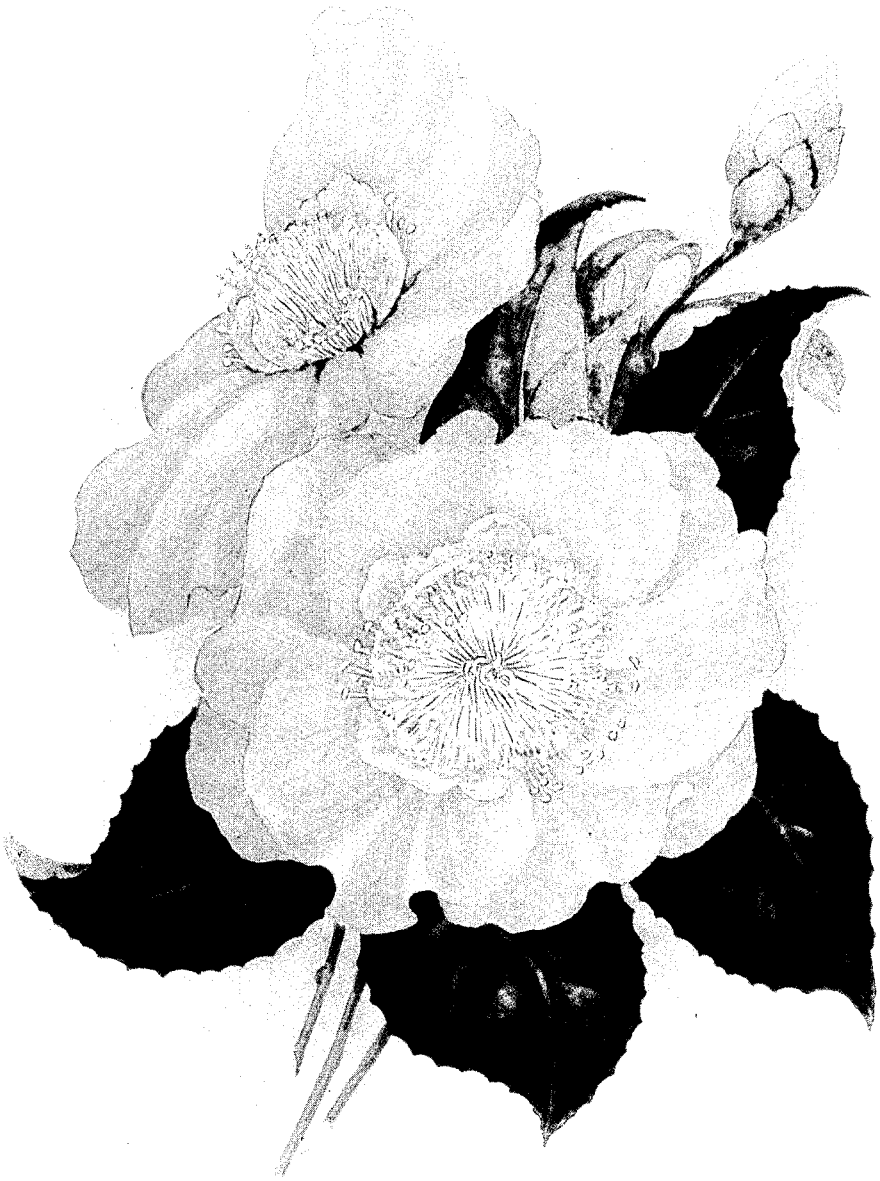
WITNESS
Addison J. Avery
INVENTOR
Rufus L. Wheeler
Wilfred E. Lawson
ATTY.

Patented Oct. 14, 1952

Plant Pat. 1,137

UNITED STATES PATENT OFFICE 1,137

CAMELLIA PLANT

Rufus L. Wheeler, Macon, Ga.

Application April 26, 1950, Serial No. 158,173

1 Claim. (Cl. 47—60)

This invention relates to a new and distinctive variety of camellia, which may be generally described as a semi-double to incomplete double form, having unusually large buds, a bloom borne singly on an unusually heavy stem and having a diameter of from five to six and one half inches and a relatively even rose color.

The parentage of the present camellia is unknown, having been obtained from a lot of several thousand chance pollinated seedlings developed by the applicant.

The development of the present camellia was brought about by the activities of applicant in collecting seeds and growing camellia plants over a number of years. Applicant, as far back as 1932, started developing camellia plants from a supply of seeds and from the original plantings some five hundred chance pollinated seedlings were obtained. From these seedlings seeds of the best plants were used to produce additional seedlings and from an eventual development of some ten thousand a selected group of approximately two hundred and twenty varieties were selected and saved in which group four outstanding plants were found, one of which is the plant of the present application. This plant first flowered in December, 1948 in applicant's nurseries where all of the preceding plant selections were made and where the reproductions by grafting were made as hereinbelow set forth.

Hand cross pollination and production of seedlings therefrom is a constant practice with applicant with a view to producing new and unusual varieties but the plant of the present application was of a chance pollinated collected seed as above set forth.

Asexual reproduction of this variety has been by grafting in Macon, Georgia.

The present new variety of camellia is further characterized by heavy convoluted guard petals and petaloids massed around the base of the stamens and petals, the stamens being heavy and in a solid circle as in Diatarin.

The colors and characteristics of the new variety of camellia comprising the invention are shown in the accompanying drawing which shows two fully opened flowers and a bud, with foliage.

A detailed description of the claimed variety of camellia is as follows:

Parentage: Seedling of chance pollination.
Classification: Botanic, camellia japonica.
Buds:
- *Size.*—Unusually large.
- *Form.*—Globular, conical.
- *Calyx sepals.*—Smooth grayish brown. Large at base, pointed.

Bloom:
- *Size.*—Five to six and one half inches in diameter.
- *Borne.*—Singly on unusually heavy stems.
- *Form.*—Semi-double to incomplete double. Three rows outer petals are regularly formed. Unusually heavy and numerous stamens form circular center. Petaloids vary in number and form at base of stamens and outer guard petals. Stamens form circular center like Diatarin.
- *Petalage.*—Three rows regular outer guard petals. Petaloids varying in size and number. Small petals to tiny petaloids, mottled white.
- *Color.*—The flower is rose in color.
- *Petals.*—Thick round or oval, smooth around edge.
- *Arrangement.*—Regular.
- *Lasting quality.*—On bush and cut flower long lasting.

Genital organs:
- *Stamens.*—Anthers; size, large; quantity, numerous. Yellow in color.
- *Filaments.*—Long, large and yellow in color.
- *Pollen.*—Yellow.

Plant:
- *Form.*—The parent plant is of rapid erect growth.
- *Growth.*—Vigorous upright branching.
- *Foliage.*—Large, average two and one half inches wide and four inches long, to four and one half inches wide and six inches long, with a distinct wave or twist as in Alba Plena.
- *Quantity foliage.*—Average.
- *New foliage.*—Reddish green distinct of variety.
- *Old foliage.*—Glossy dark green.
- *Foliage shape.*—Oval and pointed, serrated, waved and twisted.
- *Texture.*—Upper side smooth and glossy. Underside ribbed and veined.
- *Edges.*—Distinctly serrated.

Wood:
- *New wood.*—Color reddish brown.
- *Old wood.*—Rustic brown.

The color of the petals is rose close to Plate 1, letter G, #5 as described in the Dictionary of Color by A. Mertz and M. P. Paul, shading into Plate 1–K–5.

The stamens are yellow in the filaments close to the color Plate 9–C–2 of the above named dictionary with the anthers having the yellow of Plate 12–L–9.

The leaves as fully developed are dark green being close to the color Plate 24–A–12 + yellow, this color reference also being to the above stated dictionary.

I claim:

The new and distinct variety of camellia plant as herein disclosed, characterized by the flower semi-double to incomplete double, of from five to about six and one half inches in diameter, borne singly on unusually heavy stems, rose colored petals of round or oval form and smooth edges; the flower being distinguished further by having stamens forming a circular center and having large yellow anthers and long, large yellow filaments; plant of rapid, erect growth, vigorous, with foliage reddish green when new and glossy dark green when old, large averaging from two and one half to four and one half inches wide, to four to six inches long.

RUFUS L. WHEELER.

No references cited.